United States Patent [19]

Aggour et al.

[11] Patent Number: 4,499,380
[45] Date of Patent: Feb. 12, 1985

[54] APPARATUS AND METHOD FOR DETERMINING THE HYDROGEN CONTENT OF A SUBSTANCE

[75] Inventors: Mohamed A. Aggour, Houston, Tex.; Sanjoy Banerjee, Santa Barbara, Calif.

[73] Assignee: ESSO Resources Canada, Ltd., Calgary, Canada

[21] Appl. No.: 435,817

[22] Filed: Oct. 21, 1982

[51] Int. Cl.$^3$ .............................................. G01T 3/00
[52] U.S. Cl. .................................. 250/390; 250/357.1
[58] Field of Search ............... 250/357.1, 358.1, 359.1, 250/390, 391, 392

[56] References Cited

U.S. PATENT DOCUMENTS

| | | | |
|---|---|---|---|
| 2,737,592 | 3/1956 | Ohmart | 250/357 |
| 3,461,286 | 8/1969 | Jackson, Jr. et al. | 250/390 |
| 3,532,883 | 10/1970 | Dresia et al. | 250/390 |
| 3,617,735 | 11/1971 | Shoemaker | 250/357 |
| 3,688,106 | 8/1972 | Brain | 250/395 |
| 3,818,232 | 6/1974 | Kirkpatrick | 250/357 |
| 4,038,548 | 7/1977 | Charlton | 250/390 |
| 4,057,729 | 11/1977 | Hewitt | 250/390 |
| 4,251,724 | 2/1981 | Vagelatos et al. | 250/264 |
| 4,266,132 | 5/1981 | Marshall | 250/390 |
| 4,282,435 | 8/1981 | Stern | 250/390 |
| 4,381,452 | 4/1983 | Jeunehomme | 250/392 |

OTHER PUBLICATIONS

Banerjee et al., "Fast Neutron Scattering and Attenuation Technique for Meas. of Void Fractions and Phase Distri. in Trans. Flow Boiling" *Proc. Sixth Int'l. Heat Tranf. Conf.* vol. 1, 1978, pp. 351-355.

Rousseau et al., "Void Fraction Measurements During Blowdown by Neutron Absorption and Scattering Methods", *OECD/NEA Specialists Meeting*, Toronto, Aug. 1976.

Banerjee et al., "Measurement of Void Fraction and Mass Velocity in Transient Two-Phase Flow" from *Transient Two-Phase Flow*, Pergamon Press (1976).

*Primary Examiner*—Janice A. Howell
*Attorney, Agent, or Firm*—Richard F. Phillips

[57] ABSTRACT

Set forth in the accompanying disclosure is an apparatus 10 and method broadly useful for monitoring the concentration of a hydrogenous component within a given sample or space. The specific apparatus disclosed is directed to monitoring steam quality within a steam conduit 12. A fast neutron source 22 is positioned proximate a conduit 12. A moderating element 32 is situated intermediate the source 22 and conduit 12 for softening the neutron spectrum incident to the conduit 12. Two neutron detectors 36 are positioned at opposite sides of the conduit 12, each being spaced an equal radial distance from the source 22. Means 42 is provided for establishing from the rate of neutron detection and certain other physical properties of the sample data concerning the concentration or disposition of a hydrogenous component of the sample. The source 22, detectors 36, and conduit 12 are surrounded by a neutron reflector 20 of neutron moderating material.

30 Claims, 8 Drawing Figures

APPARATUS AND METHOD FOR DETERMINING THE HYDROGEN CONTENT OF A SUBSTANCE

DESCRIPTION

1. Technical Field

This invention relates generally to techniques for monitoring the concentration of a hydrogenous substance within an enclosed area. More particularly, this invention concerns an apparatus and method utilizing scattered neutron monitoring techniques for determining the relative volume fractions of steam and water passing through a conduit.

2. Background of the Invention

There are numerous situations in which it is desirable to characterize a substance by the concentration of water or some other hydrogenous material contained therein. In one class of these situations the density of the hydrogenous material is macroscopically constant across the substance and a sample of the substance may be readily isolated for analysis. Substances generally falling within this class include grain, wood, soils, slurries, etc. Where time for analysis is not limited, a sufficiently accurate measure of the concentration of hydrogenous material in such substances can generally be obtained through the use of techniques well familiar to those skilled in the art.

However, where the substance in question is at an extremely high temperature, is highly corrosive, exists only transiently or is not readily accessible, obtaining an accurate measure of the concentration of hydrogenous material therein can be difficult or impossible by traditional methods of chemical or physical analysis. One class of substances that in certain situations has proven especially resistant to common methods of analysis includes vapor-liquid mixtures such as wet steam.

It is frequently important that the steam quality at some point in a process or apparatus utilizing steam be known. Steam quality is defined as the mass ratio of the pure steam to the total fluid within a steam sample and is usually expressed as a percentage. Commonly utilized methods of measuring steam quality include sodium titration analysis, calorimetric analysis and relative volume analysis by phase separation. These methods require fluid access to the steam and are time consuming and labor-intensive. Accordingly, it has proven impracticable to provide continuous, rapid steam quality monitoring at any point in a steam system for which access to the steam itself cannot be obtained. Without such continuous rapid analysis, accurate control of steam quality often cannot be attained. Furthermore, existing methods of chemical and physical steam quality analysis are especially inadequate in certain applications due to the increasing inaccuracy of such methods with increasing steam pressure and temperature.

The use of high energy subatomic particles or electromagnetic radiation has been proposed as the basis of a non-invasive technique for monitoring various parameters of a gas-liquid sample from which the hydrogen content thereof can be determined. For example, in U.S. Pat. No. 2,732,592, issued Mar. 6, 1956, apparatus is disclosed in which the attenuation of a beam of gamma radiation of known intensity is utilized as a measure of the density of the material traversed by the beam. For measurements of gas-vapor flow through a conduit, however, this technique is of decreasing accuracy with decreasing gas-vapor bulk density. This limitation results from the interaction of gamma radiation with the conduit itself. As the density of the contents of the conduit decreases, interactions of the gamma beam with the conduit itself increasingly predominate over interactions with the contents of the conduit. It follows that a density monitoring system utilizing electromagnetic radiation or charged particles will be of limited sensitivity where the conduit itself has a beam stopping power significantly greater than that of the contents of the conduit. Thus, such systems are most inaccurate where the volume fraction of the gas within the conduit approaches 1, as is the case with high quality steam.

Systems based on neutron thermalization have recently been suggested for use in determining the concentration of a hydrogenous material within a given mixture of materials. For example, in U.S. Pat. No. 4,057,729, issued Nov. 8, 1977, a system was proposed for monitoring the amount of water within a slurry. This system included a source of fast neutrons suspended within the slurry and a thermal neutron detection system positioned within the slurry at a spaced distance from the source. From the detection rate of neutrons, the concentration of the water within the slurry can be determined. Drawbacks to such a system are that no provision is made for monitoring samples of low hydrogen density and that in many circumstances it is impracticable to position either a source or a detector within the sample.

One application for which it would be especially desirable to develop a simple, accurate and non-intrusive hydrogenous constituent monitoring system relates to steam quality monitoring for use in conjunction with steam injection systems for oil fields. It is becoming an increasingly common practice to inject high pressure, high quality steam into an oil-bearing formation to stimulate the production of oil therefrom. The injected steam serves to heat the hydrocarbons in the formation causing their viscosity to drop and, hence, their rate of flow through the formation to increase. The steam also provides a flushing action. In order to optimize the efficiency of this recovery technique, it is important that the steam quality of the injected fluid be known.

In the use of this recovery technique it is generally preferable to utilize steam having a quality greater than 70% and at a pressure of at least 11.7 MPa (1700 psi). The steam quality is preferably maintained at an optimum value dependent on the specific nature of the operation. It is desirable that an apparatus and method be provided for constantly monitoring the steam quality and, in response to deviations between the desired and the actual steam quality, to automatically adjust the operation of the steam generator to maintain the steam quality at the desired value. It is further desirable that such steam quality monitoring apparatus be non-intrusive and so constructed as to be suitable, with a minimum of adjustment, for use on any steam conduit within a wide range of configurations. It is also desirable that the apparatus and method provide results accurate at steam pressures above 11.7 MPa (1700 psi), a point beyond which most traditional methods of steam quality monitoring become either impracticable or inaccurate. It is further desirable that the apparatus and method be accurate in conditions of steam quality above 70%, where the total amount of hydrogenous material within the conduit is relatively small. The development of a practicable steam quality monitoring system and apparatus meeting these objectives will permit the more effective and efficient utilization of steam injection enhanced oil recovery techniques.

SUMMARY OF THE INVENTION

An apparatus is set forth which is useful for determining the amount of a hydrogenous substance within a given volume. The determination can be made irrespective of the phase or mixture of phases of the hydrogenous substance. From the determination of the amount of the hydrogenous substance within the given volume, subsidiary measurements (e.g. gas fraction, steam quality, liquid fraction) can be developed.

The apparatus includes a source of fast neutrons. It is important that this source not include a critical mass of fissionable material. Positioned intermediate the neutron source and the fluid mixture is a moderating material. This moderating material causes the neutrons emanating from the source in a direction toward the fluid mixture to be reduced in energy, at least a significant portion of them to within the epithermal range. A neutron detection system is positioned adjacent the fluid mixture and provides an output signal representative of the time rate of occurrence of neutron detection.

Also set forth is a method useful for determining the volume fraction of gas in a gas-liquid mixture in which at least one of the phases is hydrogenous. A flux of fast neutrons is generated from a neutron source which is free from containing a critical mass of fissionable material. A portion of these neutrons are moderated to obtain a neutron population including a significant fraction of epithermal neutrons. The gas-liquid mixture is exposed to this neutron population. A portion of the neutrons scattered by the hydrogenous material within the gas-liquid mixture are detected. The fraction of the fluid mixture which is occupied by gas is then established from the neutron detection rate and the sample pressure.

BRIEF DESCRIPTION OF THE DRAWINGS

For a better understanding of the present invention, reference may be made to the accompanying drawings, in which.

DESCRIPTION OF THE PREFERRED EMBODIMENTS

Existing methods and devices for determining the volume fraction of a particular phase of a hydrogenous material within a fluid sample are in many circumstances impractical or inaccurate. This problem is especially acute where the fluid includes high quality steam at high pressure existing in a sealed conduit under a turbulent flow regime. In one aspect of the present invention, the sample of interest is exposed to a neutron flux and a measure of the amount of hydrogenous material within the sample is obtained by monitoring the degree to which these neutrons interact with the fluid sample. The neutrons utilized issue from a fast neutron source and are moderated prior to exposure to the sample of interest to decrease the mean energy of the neutrons to which the sample is exposed. This causes neutrons scattered by the sample of interest to have a mean incident energy lower than would otherwise be the case. As a result, at low hydrogen concentrations the detected neutron count rate varies more strongly with the variations in the various volume fractions than is the case in other systems adapted for use in extreme conditions.

Figure 1:
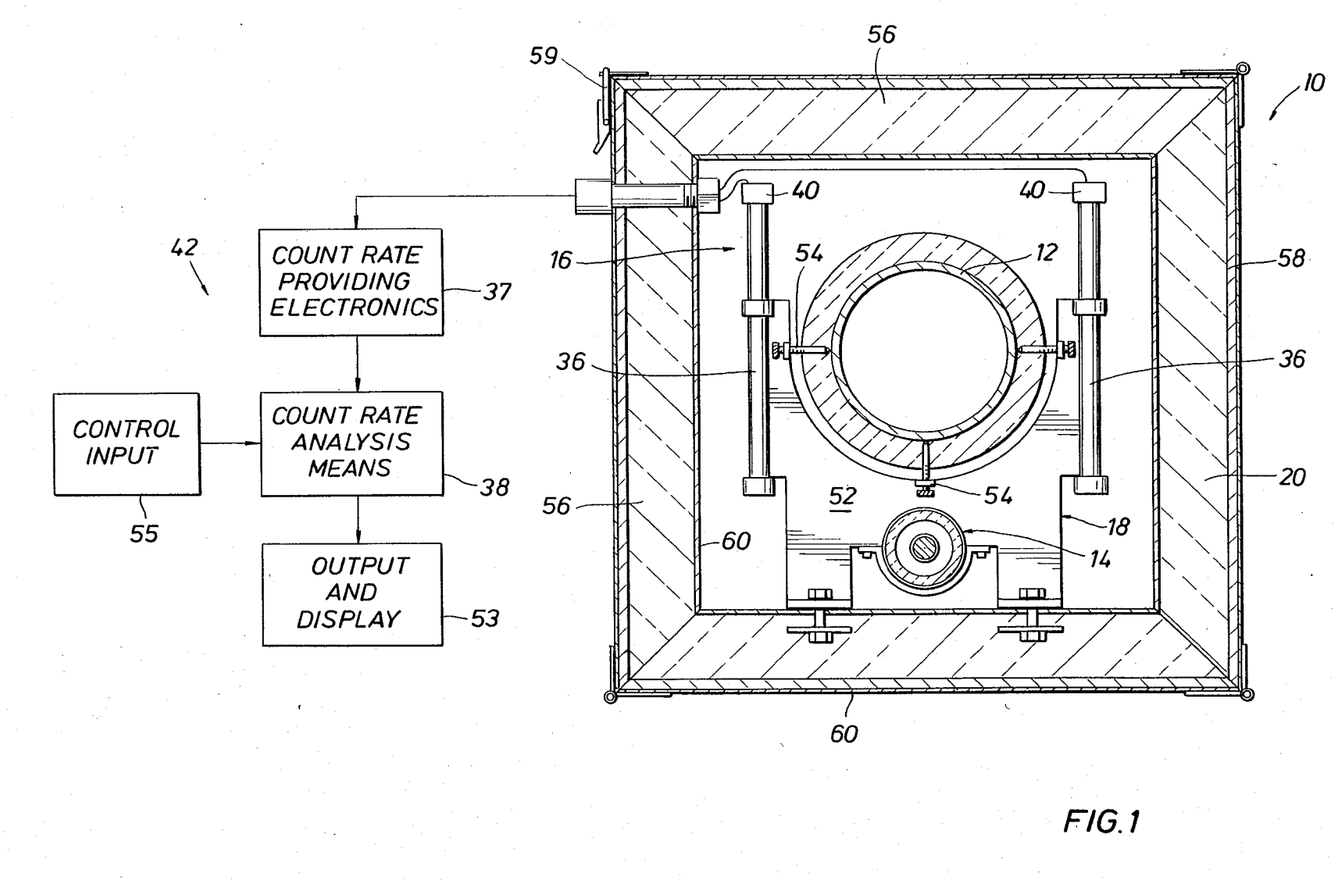
FIG. 1 shows a preferred embodiment of the present invention, this view being taken in a diagrammatic cross section along a plane transverse to the longitudinal axis of a conduit bearing the fluid mixture to be monitored.

A preferred embodiment of this apparatus for determining the amount of a hydrogenous material within a sample is depicted in FIG. 1 and is generally indicated therein by the reference numeral 10. As will be set forth below, the apparatus of the preferred embodiment is specifically adapted for monitoring steam quality. However, it is emphasized that the present invention is useful in a wide variety of applications for determining the amount of hydrogen or a hydrogenous component within a given volume or substance. For example, in another embodiment the present apparatus can be utilized to monitor the gas-fraction of a gas-hydrogenous liquid flow. For the purposes of this description and the appended claims, "water" shall mean liquid $H_2O$, "steam" shall mean the vapor phase of $H_2O$, and "$H_2O$" shall mean any of the three phases-vapor, water and ice.

The apparatus 10 of the preferred embodiment is specifically designed to monitor the quality of steam passing through a conduit 12. The basic components of this steam quality monitoring apparatus 10 include: a moderated fast neutron emitting element 14; a scattered neutron detection system 16; a support assembly 18 for positioning the neutron emitting element 14 and the neutron detection system 16 in fixed proximity to the conduit 12; a neutron reflector 20 surrounding the conduit 12 and the neutron emitting element 14; and, means 38 for converting the output of the neutron detection system 16 into a measure of steam quality.

The Neutron Emitting Element

Figure 3:
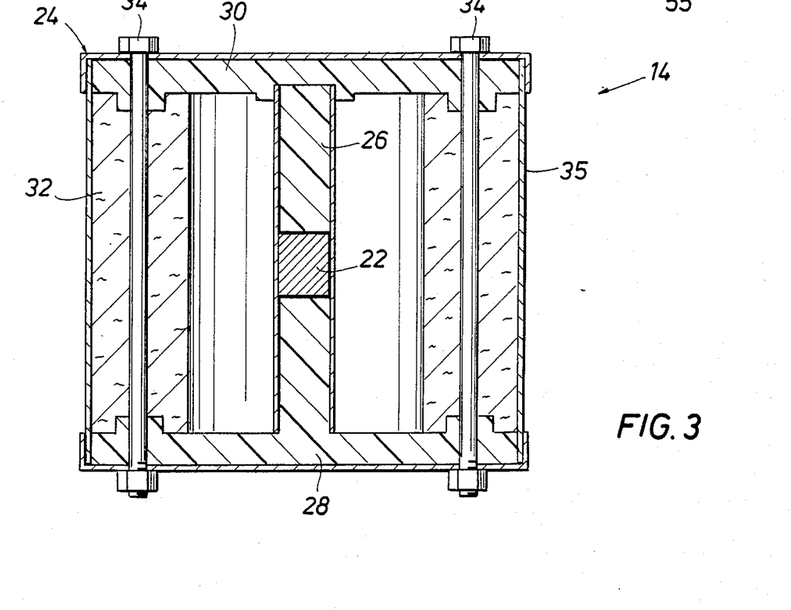
FIG. 3 shows a view taken in longitudinal cross section of a source and moderator assembly adapted for use in conjunction with a preferred embodiment of the present invention.

A preferred form of the moderated fast neutron emitting element 14 is best shown in FIG. 3, which is a cross sectional view taken along the longitudinal axis of the generally cylindrical neutron emitting element 14. A fast neutron source 22 is positioned within a protective, encapsulating neutron source housing 24. The fast neutron source 22 is preferably composed of 2 millicuries of Californium-252. Alternatively, this source could be a 1 curie Americium-Beryllium source, a Polonium-Beryllium source, or some other suitable source of fast neutrons as would be familiar to those skilled in the art. It is preferred that Californium-252 be utilized as the fast neutron source because its neutron spectrum is softer (that is, of a generally lower mean kinetic energy) than that of most other practicable neutron sources. In addition, the physical volume of Californium-252 required to obtain a given neutron flux is smaller than that of most other neutron sources. This provides benefits in the encapsulation and mounting of the source 22.

It is preferred that the source 22 either not include fissionable material or, if it does include fissionable material, that the fissionable material be present in an amount less than the minimum required mass for criticality. Thus, the neutron source 22 should be free from including a critical mass of fissionable material. This provides obvious advantages relative to radiological safety.

The neutron source housing 24 includes a central support portion 26 which encapsulates and supports the fast neutrons source 22. There are flanges 28, 30 at opposed ends of the central support portion 26. At least one of these flanges 30 is removable from the central support portion 26. The flanges 28, 30 are adapted for receiving a generally cylindrical moderating element 32. Fasteners 34 extending between the flanges 28, 30 are utilized to secure the integrity of the fast neutron emitting element 14 following insertion of the moderating element 32.

In the preferred embodiment the fast neutron emitting element 14 is adapted to permit moderating elements 32 of varying wall thicknesses to be selectively interposed intermediate the flanges 28, 30 and surrounding the fast neutron source 22. This permits the degree of moderation of the neutrons emanating from the fast neutron source 22 to be selectively variable. This is desirable from the standpoint of rendering the apparatus 10 easily adaptable to a wide variety of situations. It has been found that for most applications the thickness of a hydrogenous moderating element 32 should be at least equal to the mean free path for hydrogen scattering of 0.1 MeV neutrons. This is approximately equivalent to a 1 cm thickness of water.

The preferred composition of the moderating element 32 is polymerized methyl methacrylate, available under the trademark "Lucite". Other materials having high hydrogen densities and relatively low macroscopic neutron capture cross sections are also acceptable. For example, the moderating element 32 could be fashioned of paraffin wax or a polymeric material such as polyacrylate or polyolefin. It is desirable that the flanges 28, 30 and central support portion 26 of the fast neutron source housing 24 also be fashioned of a material having a significant neutron moderation ability. It is further desirable that the material from which the remainder of the fast neutron source housing 24 is made provide significant structural integrity. A suitable such material is ultra-high molecular density plastic. A thermal neutron absorbing material 35 encloses the fast neutron source housing 24 and the moderating element 32. Preferably, this thermal neutron absorbing material 35 is a jacket of Cadmium 3-6 mm in thickness.

Neutron Moderation

The moderation of the neutrons emitted from the fast neutron source 22 prior to exposure of the steam conduit 12 to the resulting neutron flux is an important aspect of the present apparatus. The purpose of this neutron moderation is not to increase the neutron flux at the conduit 12. Neutrons will enter the steam conduit 12 from the fast neutron source 22 irrespective of whether or not they have been moderated to some extent prior to exposure to the steam conduit 12. In fact, from a neutron source of a given strength, a greater fraction of the neutrons will reach the steam within the conduit 12 if they are not moderated than if they are moderated. However, we have discovered that if the neutrons to which the conduit 12 is exposed are properly moderated not only does the incidence of neutron detection increase, but also the fractional sensitivity of the count rate to the amount of hydrogen within the conduit is significantly improved for relatively low concentrations of hydrogen. This is true even though the magnitude of the neutron current entering the conduit 12 is lower for the case of the moderated source. This increase in sensitivity and in detection rate provides important improvements in the accuracy of monitoring relatively small amounts of a hydrogenous substance within a conduit, such as in the case of high quality steam As a population of neutrons interacts with a moderating material, such as hydrogen, its mean energy decreases. In the present invention, as will be explained subsequently, the degree of interaction of the neutrons with the water and steam within the conduit 12 is a direct function of the mass of the water and steam in the conduit 12. Importantly, for the type of neutron detectors most often utilized in applications involving neutron scattering from a hydrogenous material, the detector efficiency is inversely related to the energy of the neutrons. It follows, then, that the neutron detection rate will increase as the amount of $H_2O$ within the conduit 12 increases. That is, for a neutron source of given strength there is a direct relationship between the rate of neutron detection and the concentration of hydrogen within the sample under consideration. This is one of the principles upon which is based measurements of hydrogen density by the scattered neutron monitoring technique.

Neutrons are emitted from the fast neutron source 22 due to the spontaneous fission of the Californium-252 nuclei. A significant amount of energy is also released in this event. Much of this released energy takes the form of kinetic energy of the neutrons. The precise magnitude of the energy carried off as velocity of the neutron varies from fission event to fission event. The range of these energies for the fission of Californium-252 varies between about 0.1 and 8 MeV with a mean neutron energy equal to about 2.2 MeV. 1 Mev=$1\times10^6$ eV, where 1 eV, the abbreviation for electron-volt, is defined as the energy gained by an electron as it is accelerated across an electric potential of one volt. Neutrons having kinetic energies in excess of 1 keV are typically referred to as "fast neutrons". Thus, Californium-252 is a fast neutron source. Most other practicable neutron sources have a somewhat higher mean neutron emission energy than does Californium-252.

As neutrons travel from their point of origin they collide with the nuclei in their path. Each collision results in one of three events: capture of the neutron by the target nucleus, this occurrence being termed absorption; temporary capture and subsequent ejection of the neutron by the nucleus, this being termed inelastic scattering; and, elastic scattering of the neutron away from the nucleus. The neutrons emitted from a neutron source initially have energies far in excess of those of the nuclei of the substance through which they pass. Thus, as these fast neutrons collide with the target nuclei in a scattering event, they lose a portion of their kinetic energy to the nuclei. After a sufficiently great number of scattering events the neutrons will have lost their excess energy and will travel at a mean velocity dictated by the temperature of the medium through which they are passing. Such neutrons are then in thermal equilibrium with their environment and accordingly are known as thermal neutrons. Neutrons in thermal equilibrium with a substance at 20° C. have a mean energy of about 0.025 eV. Thermal neutrons are defined herein as neutrons having energies below about 0.3 eV. Neutrons having energies intermediate the thermal and fast ranges are referred to as epithermal neutrons.

Following their emission from the neutron source 22, fast neutrons will lose energy through scattering, as previously discussed, and will finally be absorbed by some nucleus. This process of energy loss through scattering is termed moderation. Neglecting for the moment inelastic scattering, which in any event has only a small influence at neutron energies of less than 2 MeV, the neutron moderation process can be described to a very good approximation by Newtonian physics. That is, in each scattering event between a neutron and a target nucleus both momentum and energy are conserved. Accordingly, neutrons are moderated to the greatest extent per interaction by hydrogen nuclei. This is because hydrogen nuclei are of a mass almost equal to that of a neutron. The greater the atomic number of a nucleus, the poorer a moderator it makes. A 2 MeV neutron requires only about 18 interactions with hydrogen nuclei to attain thermal equilibrium with its surroundings. However, to reach an equivalent degree of moderation in a sample of iron would require over 500 interactions. Neglecting the effects of absorption, in virtually all hydrogenous substances, water included, the effect upon neutron moderation of all nuclei other than hydrogen is minor. This is not to say that neutrons have a greater chance of interacting with a hydrogen nuclei than with any other nuclei, for this is often not the case, but rather that high energy neutrons typically lose a much greater fraction of their energy in scattering from hydrogen than from any other nuclei.

The probability of interaction of a neutron in traversing a given thickness of some material is a function both of the density and composition of the material and of the energy of the neutron. This probability of interaction is related to the macroscopic cross section of the target material. The macroscopic cross section of a substance is the inverse of the mean free path of neutrons of a certain energy in that substance. For a given substance and at a given neutron energy the macroscopic cross section of that substance is directly proportional to the density of that substance. The macroscopic scattering cross section of most materials, including hydrogen, increases gradually with decreasing neutron energy. The macroscopic absorption cross section of most materials increases strongly with decreasing neutron energy. For example, the macroscopic neutron absorption cross section of Cadmium increases by a factor of 3000 as the neutron is moderated from 2 eV to 0.2 eV.

The Neutron Detection System

The neutron detection system 16 includes a pair of neutron detectors 36. These detectors 36 are preferably positioned such that a line joining the midpoint of each of the detectors 36 passes through the center of the conduit 12 and is perpendicularly bisected by the plane defined by the center of the fast neutron source 22 and the longitudinal axis of the conduit 12. Such an arrangement is shown in FIG. 1. While it is not essential that the detectors 36 each be positioned precisely 90° from the fast neutron source 22, it is important that the radial spacing, relative to the longitudinal axis of the conduit 12, from the fast neutron source 22 to each of the detectors 36 be equal.

The use of a pair of detectors 36 disposed symetrically relative to the combination of the fast neutron source 22 and the conduit 12 serves to minimize errors arising from improper detector placement and from flow regimes asymetric relative to the source-conduit combination. As will be explained subsequently, an invariable detector to detector spacing is accurately maintained by the support assembly 18. Thus, if one of the detectors 36 records an artificially great rate of neutron detection due to being positioned too close to the conduit 12, the other of the detectors 36 will be positioned corresponding distance farther from the conduit 12 than it should and will detect commensurately fewer neutrons. By averaging the count rates of the two detectors 36, the system is rendered substantially insensitive to error arising from improper detector placement. Similarly, where the flow regime within the conduit 12 causes a disproportionately great amount of water to be situated near one of the detectors 36, the neutron detection rate of that detector would reflect a greater water content within the conduit 12 than would actually be the case. However, such a flow regime would also cause the other of the detectors 36 to indicate too low a water content. Accordingly, the average of the detector outputs is substantially insensitive to anomalies in flow pattern.

The neutron detectors 36 are Helium-3 type proportional counters. These detectors 36 preferably have a cross-sectional chamber area of about 4.8 cm$^2$ and are pressurized to 4 atmospheres. The detection efficiency of such detectors is strongly dependent upon neutron energy, being more than two orders of magnitude more efficient for thermal neutrons than for 100 eV neutrons. The selectivity of Helium-3 type neutron detectors for thermal neutrons increases with decreasing chamber pressure. However, decreasing the chamber pressure of the detector 36 also brings about a decrease in detection efficiency.

Figure 2:
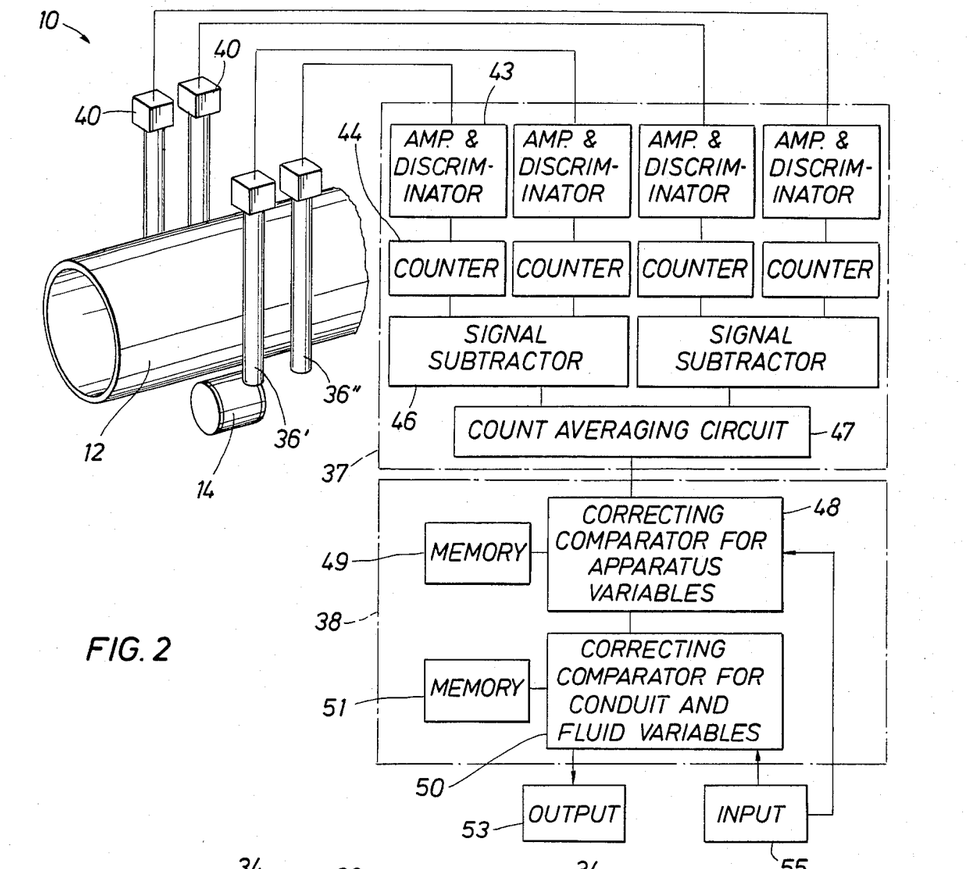
FIG. 2 shows a diagrammatic representation of a detector output discriminator, counter and analysis system for converting the output of the detectors into a signal related to either the steam quality, the hydrogen content or the gas volume fraction of the fluid within the conduit.

The sensitivity of the present steam quality monitoring means 10 can be somewhat improved by eliminating the effects of epithermal and fast neutrons on the counting rate. This is accomplished through the use of a neutron detection system 16' having a pair of detectors 36', 36" at each detection location, as shown in FIG. 2. The detectors 36', 36" of each detector pair abut one another along a plane which passes through the fast neutron source 22 and which is perpendicular to the longituninal axis of the steam conduit 12. One of these two detectors 36' is encased in a thin shield of Cadmium and consequently is sensitive substantially only to epithermal and fast neutrons. The second detector 36" is not provided with the Cadmium shield, but is otherwise identical to the first detector 36'. By subtracting the count rate of the first detector 36' from that of the second detector 36", the detection rate of thermal neutrons is established.

The neutron detection system 16 also includes means 37 for establishing the average neutron detection rate. Receiving the output of the neutron detection system 16 is means 38 for determining steam quality from analysis of the neutron detection rate by the detection system 16. The neutron count rate analysis means 38 serves to correct the count rate for certain variables and to calculate the steam quality from this corrected count rate. It is to be understood that while in the preferred embodiment the count rate analysis means 38 provides a measure of the steam quality within the conduit 12, in other embodiments the count rate analysis means 38 could be adapted to provide, for example, a measure of volume fraction of a given phase in a gas-liquid mixture, or mass of hydrogen per unit volume of an enclosed area.

The Count Rate Analysis Means

As best shown in FIG. 2, each detector 36 is provided with a preamplifier 40, preferably positioned as near the detector electrode output as is possible. The output of this preamplifier 40 is supplied to a control, analysis and output assembly 42 (FIG. 1) situated a spaced distance from the fast neutron source 22 and detectors 36. In the preferred embodiment, the control and analysis assembly 42 contains the neutron detection rate providing means 37 and the neutron count rate analysis means 38 along with their associated components, as will be described subsequently.

An amplifier and discriminator assembly 43 receives the preamplified output of each detector 36. The output of each amplifier and discriminator assembly 43 is provided to a pulse counter 44. For the alternative embodiment utilizing detector pairs 36', 36" for eliminating the effects of detected epithermal and fast neutrons, a signal subtractor 46 is provided for subtracting the count rate of the first detector 36' from the second detector 36" of each detector pair. Finally, the neutron detection system 16 includes a count averaging circuit 47 for providing an output directly related to the average of the inputs received from each detector pair 36', 36" or individual detector 36.

The neutron count rate analysis means 38 receives the output of the average neutron detection rate providing means 37 and establishes from this an output representative of the steam quality. The count rate analysis means 38 includes a correcting comparator for apparatus variables 48 and a correcting comparator for conduit and fluid variables 50. The correcting comparator for apparatus variables 48 receives inputs concerning the various variables related to the monitoring apparatus 10 itself and provides a count rate corrected for these variables. The variables for which a correction is applied by the correcting comparator for apparatus variables 48 include detector efficiency, apparatus temperature, and source strength. These can vary with time and other factors. Associated with the correcting comparator for apparatus variables 48 is a first memory 49. In the preferred embodiment an input 55 is provided for use in inputting detector efficiency, detector pressure, source age and apparatus temperature. Alternatively, certain of these variables could be monitored and corrections therefor applied automatically and continuously. In response to receiving inputs as to these factors, the correcting comparator for apparatus variables 48 reads the first memory 49 to obtain the requisite correction and then effects this correction. The output of the correcting comparator for apparatus variables 48 is a corrected count rate.

The output of the correcting comparator for apparatus variables 48 is provided to the correcting comparator for fluid and conduit variables 50. The correcting comparator for fluid and conduit variables 50 receives inputs concerning the condition of the steam and conduit configuration and provides as an output the steam quality. Alternatively, as set forth previously, the correcting comparator for conduit and fluid variables 50 can provide an output other than steam quality, such as the conduit volume fraction occupied by gas. The inputs of importance for which a correction is applied by the correcting comparator for conduit and fluid variables 50 are, the slip ratio (the ratio of the vapor flow rate to the liquid flow rate within the conduit 12), the conduit diameter, and the conduit pressure or temperature.

It is necessary to know either the steam pressure or temperature in order to calculate the steam quality once the amount of $H_2O$ within a given length of the conduit 12 is known. Since the steam is saturated, it is not necessary to know both of these variables. Preferably, the monitored variable is temperature. To obtain the temperature, one or more of the set pins 54 (detailed subsequently) are provided with a thermocouple (not shown) at a position in contact with the conduit 12. A recess (not shown) may be drilled a distance into the wall of the conduit 12 to yield a more accurate measure of the steam temperature. The output of this thermocouple is provided directly to the correcting comparator for fluid and conduit variables 50. The accuracy of this method of measuring the temperature of the wet steam passing through the conduit 12 is increased by surrounding the conduit 12 and set pin 34 with an insulative material as is shown in FIG. 1.

The correcting comparator for fluid and conduit variables 50 includes a second memory 51, which can take the form of a ROM, in which is stored a plurality of tables of raw steam quality as a function of observed count rate for various conduit diameters. Interpolative techniques are utilized where the conduit size is intermetiate values provided by the existing tables. A correction for pressure is then applied. Following this, the correction for the slip ratio is made to the pressure corrected raw steam quality to yield the actual steam quality. Details of the various variables of relevance to the correcting comparator for conduit and fluid variables 50 are provided at the input 55. Certain of these variables can be monitored and input automatically.

The Support Assembly

The support assembly 18 serves to fix the steam quality monitoring means 10 to the conduit 12 and to support the various elements of the monitoring means 10 in the correct orientation relative to one another. It is especially important that the support assembly 18 be adapted to ensure that the detectors 36 and the fast neutron source 22 are oriented and spaced with precision relative both to the conduit 12 and to each another. As shown in FIG. 1, the support assembly 18 includes a rigid mounting frame 52 to which the neutron emitting element 14 and detectors 36 are fixedly attached. The mounting frame 52 includes set pins 54 adapted to extend through any insulation which may surround the conduit 12. These set pins 54 are adjustable to allow both precise control over the source to conduit distance and equal conduit to detector spacing.

In the preferred embodiment a Cadmium-lined neutron reflector 20, best shown in FIG. 1, is positioned surrounding the fast neutron source 22, the detectors 36 and the conduit 12. The term "surrounding" as utilized in describing the spatial relationship of the reflector 20 to the conduit 12 is intended to indicate that the neutron reflector 20 provides a radial enclosure of a section of the conduit 12. The reflector 20 must, of course, include apertures through which the conduit 12 extends. The reflector 20 preferably includes paraffin slabs encased in a structurally supportive metallic case 58. Alternatively, any good moderating material could be utilized in place of paraffin. The reflector 20 is hinged to permit access to the mounting frame 52. The inner and outer faces of the reflector 20 are lined with Cadmium sheeting 60 to prevent thermal neutrons from passing into or out of the reflector 20.

The support assembly 18 is provided with apparatus (not shown) for clamping the support assembly 18 to the conduit 12. Following adjustment of the position of the mounting frame 52 relative to the conduit 12, the reflector 20 can be closed and secured with a latch 59. It has been discovered that in the use of the present invention, improved results are obtained by mounting the support assembly 18 such that the neutron source 22 is positioned on the gravitationally downward side of the conduit 12.

Figure 8:
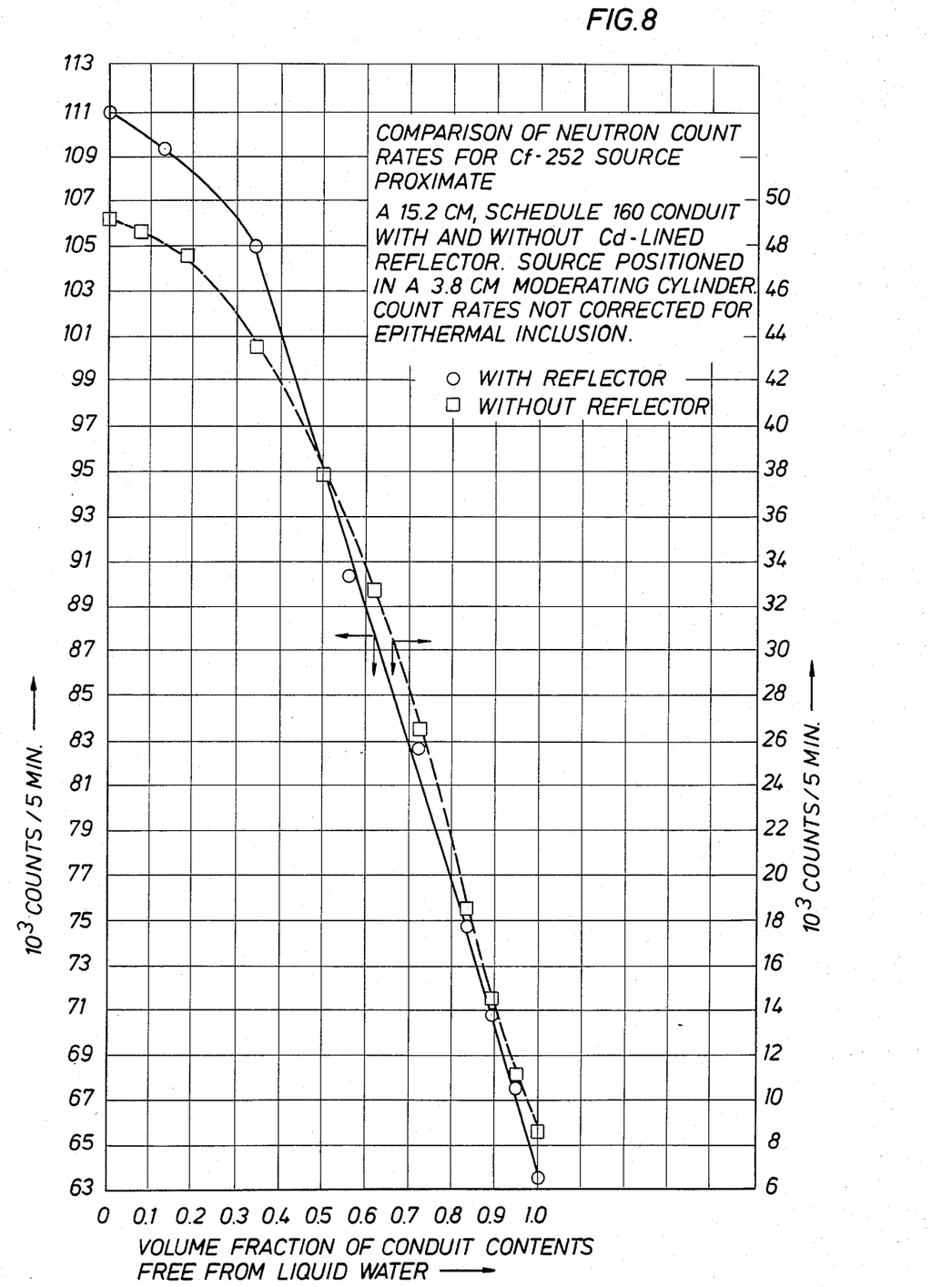

It has been found that the Cadmium-lined neutron reflector 20 provides two significant benefits. First, acting as a neutron reflector, the reflector 20 reflects back into the steam conduit 12 many epithermal and fast neutrons that otherwise would have entirely escaped the apparatus 10. This improves the utilization of the fast neutron source 22 avoiding the need for as strong a neutron source as would otherwise be required. The increase in neutron detection rate caused by the use of the neutron reflector 20 is clearly indicated by the experimental results set forth in FIG. 8. To minimize the detection of neutrons moderated within the reflector 20 and scattered directly to a detector 36, it is desirable to utilize the epithermal insensitive detector detection system 16 detailed previously. Second, the Cadmium-lined reflector 20 serves to minimize error originating from neutrons leaving the vicinity of the conduit 12, being thermalized and then reflected back into the conduit 12 or detectors 36. The need for this was appreciated when, during a test of the system, unusual results were obtained following a heavy rain. It was theorized that the water-soaked soil adjacent the steam conduit 12 served to thermalize and reflect neutrons back to the system, significantly skewing the results obtained.

The preferred embodiment provides important benefits relative to radiological safety. As previously detailed, the fast neutron source 22 is surrounded by a moderating element 32 and a neutron source housing 24. This softens the mean energy of neutrons emanating from the neutron source 22 thereby reducing the radiological quality factor of the neutrons utilized practicing in the present invention. This permits the use of a lesser amount of external neutron shielding than would otherwise be required to attain a given safe radiation exposure level. Also, the use of source moderation coupled with Cadmium shielding decreases the number of neutrons released to the environment in the practice of the invention. Further, the thermal neutron absorbers 35, 60 surrounding the source 22 and lining the reflector 56 decrease the flux of thermal neutrons in the vicinity of the conduit 12. This minimizes the extent to which the conduit 12 is activated.

Experimental Results

Experiments were performed to establish the sensitivity of the present invention. The results of these experiments are set forth in FIGS. 4-8. In each test a pair of 2.5 cm internal diameter, Helium-3 proportional neutron detectors pressurized to four atmospheres was utilized in an arrangement similar to that shown in FIG. 1. The sample utilized was air and water contained within a conduit 12. The conduit 12 was situated horizontally with the neutron emitting element 14 positioned gravitationally downward from the conduit 12. The use of an air and water sample was desirable because it permitted the amount of hydrogen within the conduit 12 to be measured and controlled with great precision. Californium-252 was utilized as the fast neutron source 22. For those instances in which the source 22 was moderated, the moderator utilized was a cylinder of Lucite. Whether or not moderated, the source 22 was enclosed in a Cadmium jacket.

Figure 4:
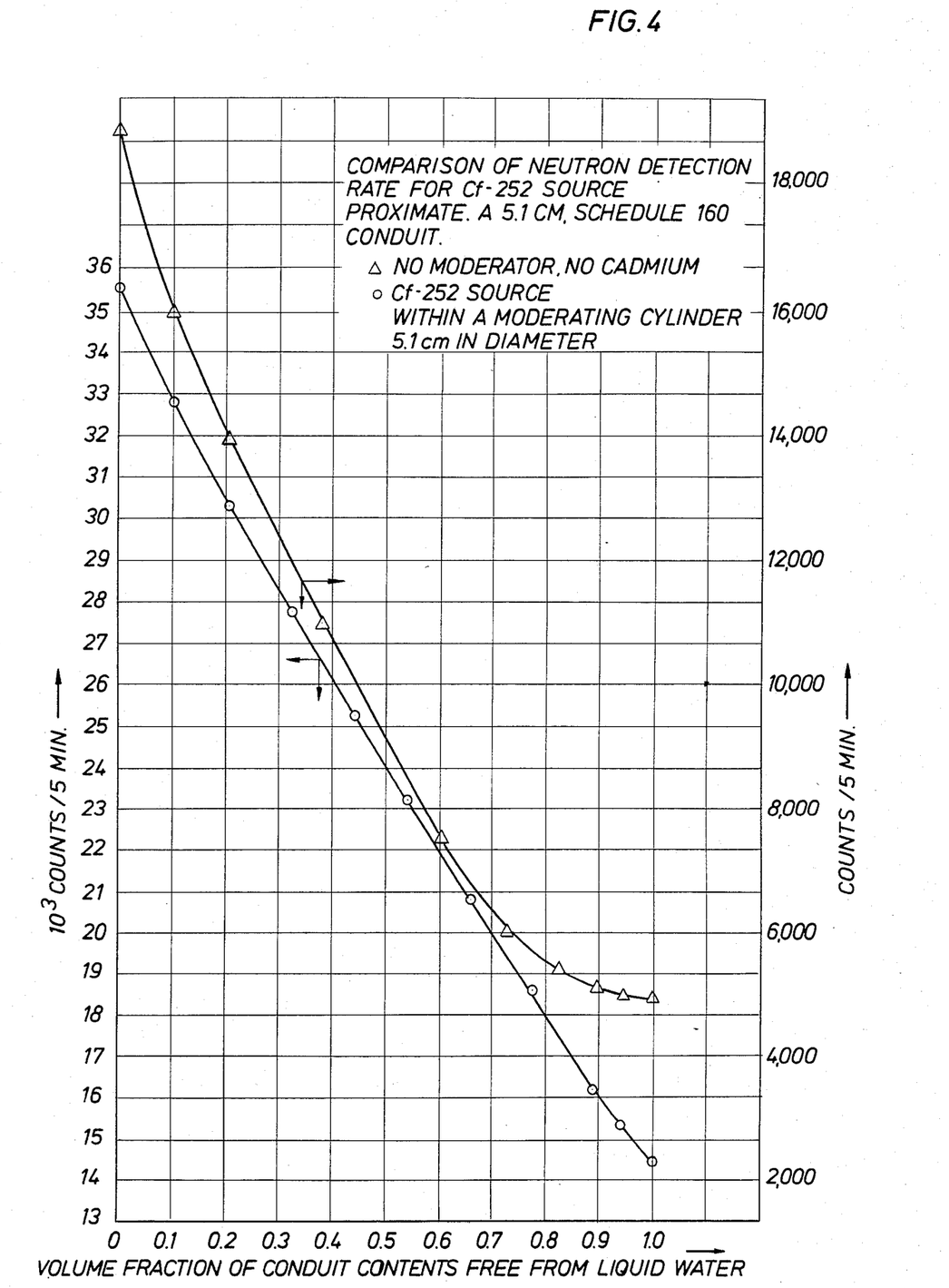
FIG. 4 is a graph relating neutron count rate to the volume fraction of gas within a water-bearing conduit for two experiments having identical source, conduit and detector configurations but in one of which the neutrons spectrum is softened through the use of moderating material prior to exposure to the conduit.

FIG. 4 provides a graphical representation of the rate of neutron detection as a function of conduit void fraction for both a moderated and an unmoderated source. This comparison clearly indicates that all other factors being equal, the neutron detection rate is more than doubled by the use of a moderated source. Even more significant is the improvement in linearity of the count rate/volume fraction relationship derived from the use of a moderated source. Further, the use of a moderated source rather than an unmoderated source is shown to be especially beneficial at void fractions approaching 1, this range of void fractions corresponding to high steam quality. These experimental results clearly indicate that the sensitivity to hydrogen content of the moderated system is about three times as great as that of the unmoderated system for void fractions greater than 0.9.

Figure 5:
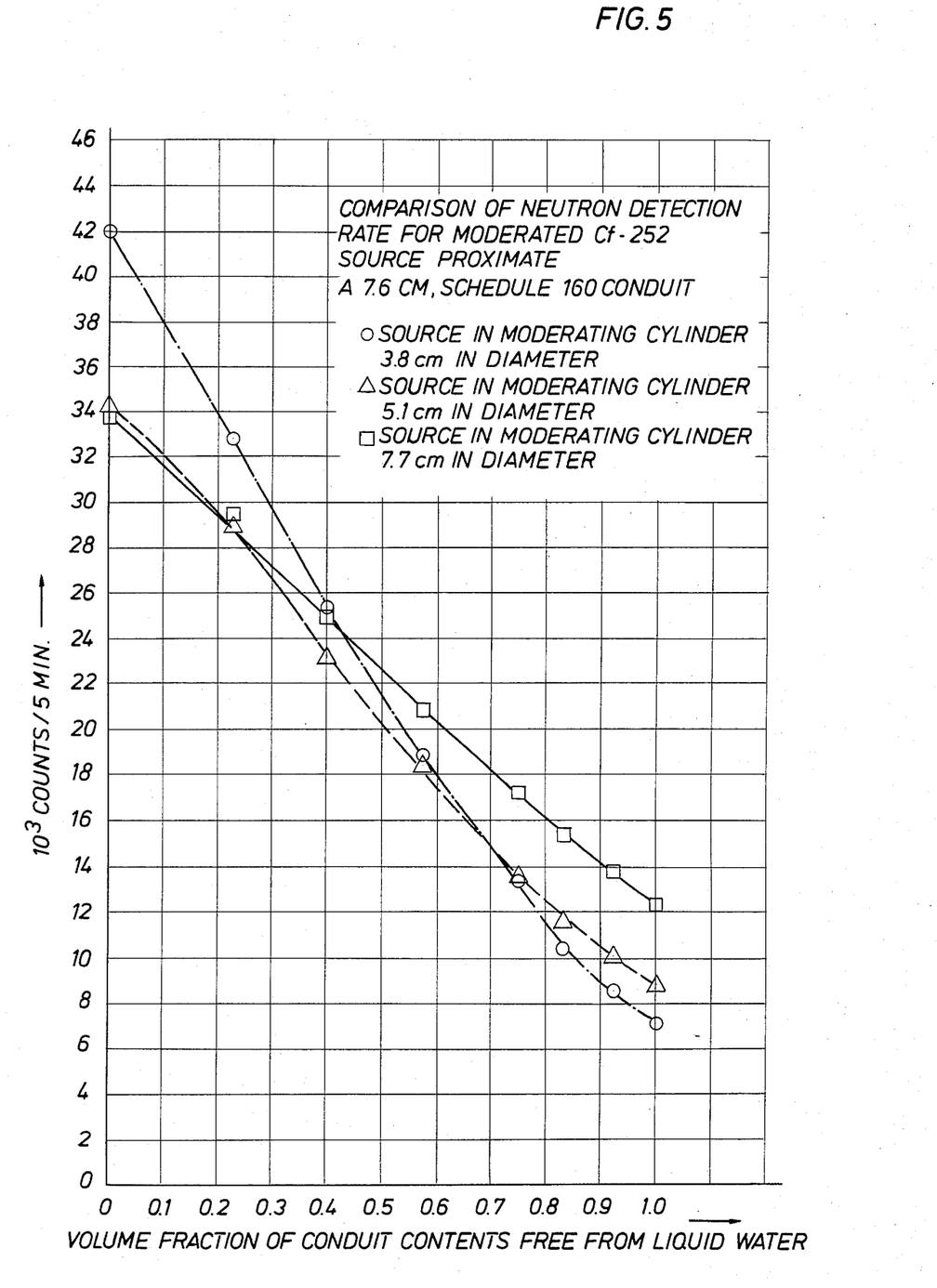
FIGS. 5–7 show the effect of the use of varying amounts of moderating material and conduits of differing sizes on the relationship between neutron count rate and the volume fraction of gas within a water-bearing conduit; and, FIG. 8 shows the effect on the relationship between neutron count rate and conduit void fraction of the use of a neutron reflector surrounding the source, conduit and detectors.
Figure 6:
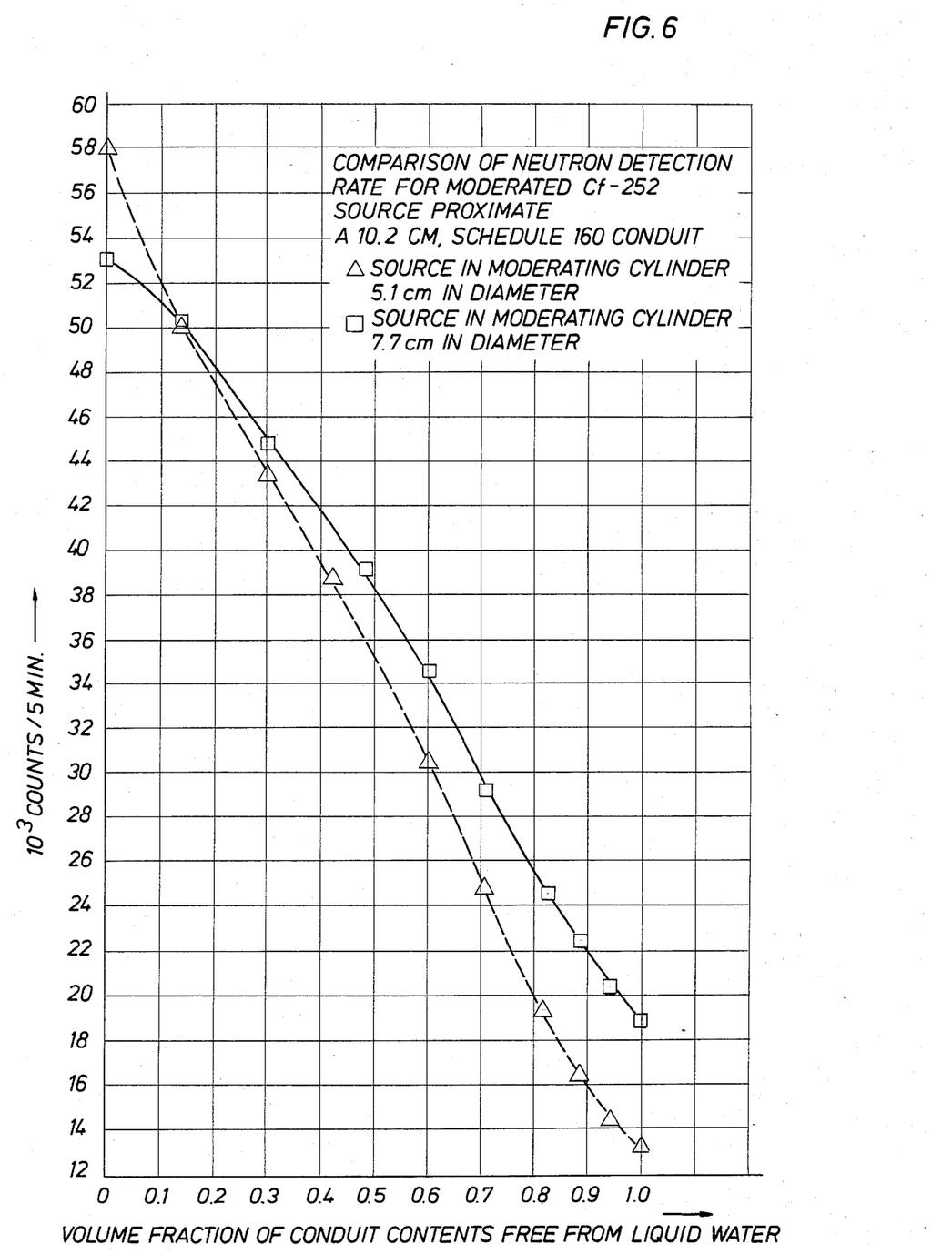
Figure 7:
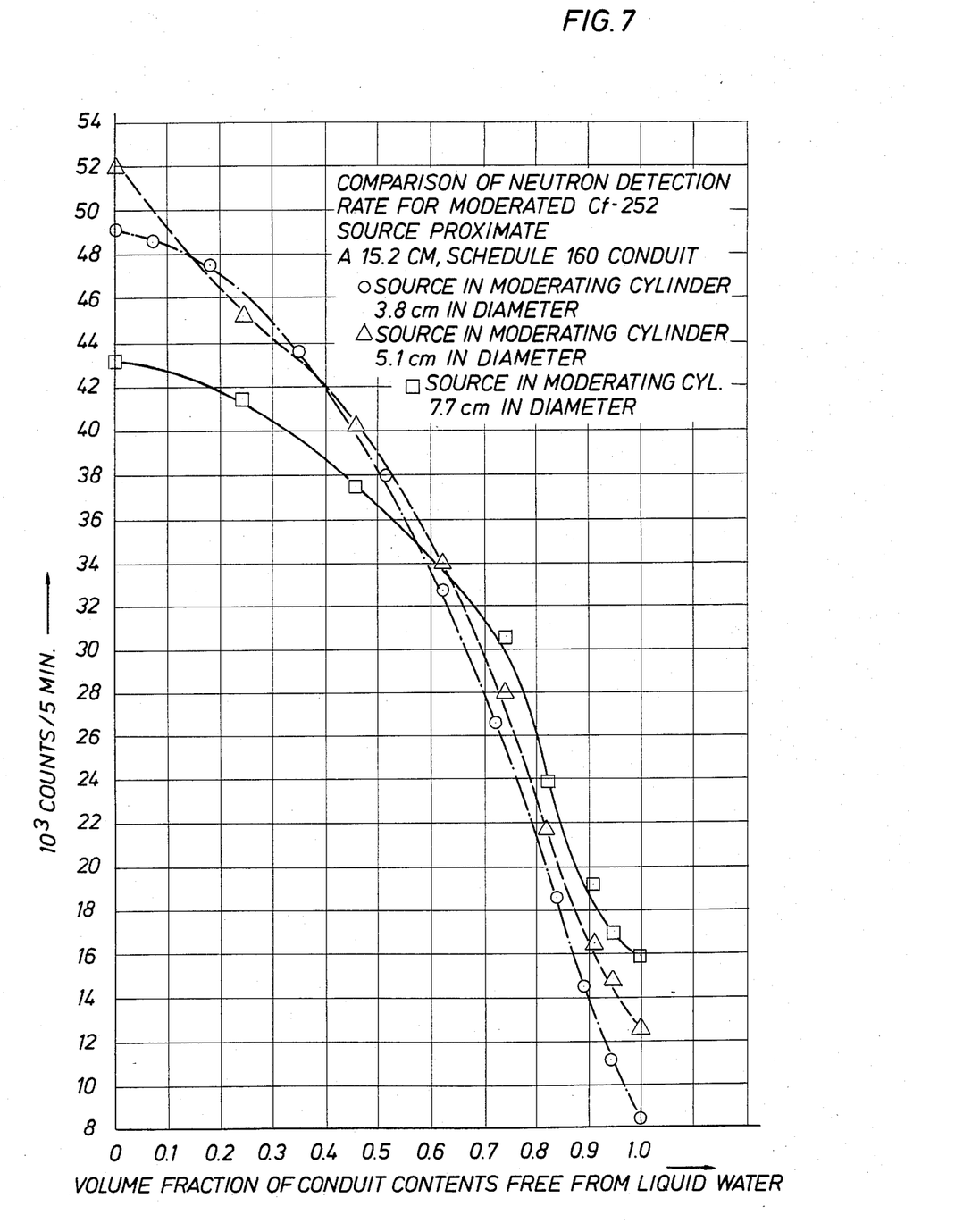

FIGS. 5-7 each provide the relationship between neutron detection rate and void fraction for varying degrees of source moderation. FIGS. 5-7 relate, respectively, to conduits having diameters of 7.6 cm, 10.2 cm, and 15.2 cm. These graphs show that as the conduit size increases, the degree of source moderation required to achieve the optimum measure of sensitivity and linearity to hydrogen content in the high void fraction region generally decreases.

Additional experiments were performed to establish the accuracy of this apparatus and method in monitoring the quality of actual steam. From the results set forth in FIGS. 4-7, the theoretical relationship between neutron count rate and steam quality was obtained for each of the conduit and moderator sizes. Then, for each of the tested conduit sizes (5.1 cm, 7.6 cm, 10.2 cm, and 15.2 cm, Schedule 160 conduit) steam of quality ranging from 5% to 95% was monitored with the present apparatus. A measure of the true steam quality was obtained through use of tedious, albeit relatively accurate, sodium-titration techniques well known to those skilled in the measurement of steam quality. The agreement between results obtained by the present apparatus and by the sodium-titration technique was excellent.

The present invention and the best mode in which it is contemplated have been described. It is to be understood that the foregoing is illustrative only and that other means and techniques can be employed without departing from the true and full scope of the invention as described in the appended claims.

What is claimed is:

1. Apparatus for providing an output corresponding to the amount of hydrogenous material within an enclosure, comprising:

13 a fast neutron source, said fast neutron source being positioned proximate said enclosure and being incapable of achieving criticality;

moderating material positioned intermediate said enclosure and said fast neutron source, said moderating material having a neutron moderating ability at least equivalent to that of a 1 cm thickness of water; and a neutron detection system including at least one neutron detector positioned proximate said enclosure, said neutron detection system being adapted to provide an output signal representing the rate of detection of neutrons scattered from said hydrogenous material.

2. The apparatus of claim 1 further comprising a thermal neutron shield interposed intermediate said at least one neutron detector and said moderating material.

3. The apparatus of claim 2 further comprising a neutron reflector positioned around the combination of said fast neutron source, said at least one neutron detector and said enclosure.

4. The apparatus of claim 3 further comprising a second thermal neutron shield positioned intermediate said neutron reflector and said at least one neutron detector.

5. The apparatus of claim 3 wherein said reflector is composed of a hydrogenous material having a neutron moderating ability at least equivalent to that of 3 cm of water.

6. The apparatus of claim 2 wherein said enclosure is symetrically disposed about a longitudinal axis and wherein said neutron detection system includes two neutron detectors, said neutron detectors being symetrically disposed about a plane defined by the geometric center of said fast neutron source and the longitudinal axis of said enclosure, and wherein said neutron detectors have a higher neutron detection efficiency for thermal neutrons than for epithermal neutrons.

7. The apparatus of claim 6 wherein a line joining the geometric center of said detectors intersects the longitudinal axis of said enclosure.

8. The apparatus of claim 7 wherein neutron detectors each include two detection chambers.

9. The apparatus of claim 4 wherein both said first and said second thermal neutron shields are adapted for capturing substantially all neutrons incident thereto having energies in the range of from zero eV to a first energy and said neutron detection system is substantially insensitive to neutrons having energies greater than said first energy.

10. The apparatus of claim 2 wherein said thermal neutron shield is adapted for capturing substantially all neutrons incident to it having energies in the range of from zero eV to a first energy and said neutron detection system is substantially insensitive to neutrons having energies greater than said first energy.

11. A device for monitoring the amount of $H_2O$ within a portion of a conduit, comprising:

a source of fast neutrons, said source of fast neutrons being positioned proximate said conduit and being free from including a critical mass of fissionable material;

means for moderating neutrons entering said conduit from said fast neutron source prior to said neutrons reaching said conduit, said moderating means having a neutron moderating ability at least equivalent to that of a 1 cm thickness of water;

14 means for detecting neutrons, said neutron detecting means having a higher detection efficiency for thermal neutrons than for epithermal neutrons, said neutron detecting means including at least one neutron detector positioned adjacent said conduit and at a spaced distance from said fast neutron source; and, shielding means for substantially preventing neutrons having energies of less than 0.4 eV from traveling from said moderating means to said conduit and said neutron detector.

12. The $H_2O$ quantity monitoring device of claim 11 further comprising a neutron reflector surrounding the combination of said fast neutron source, said moderating means, said conduit and said at least one neutron detector.

13. The $H_2O$ quantity monitoring device of claim 11 wherein a reflected thermal neutron shield is positioned interior to said neutron reflector, said reflected neutron shield surrounding the combination of said moderating means, said at least one neutron detector, said conduit and said fast neutron source, said reflected thermal neutron shield being adapted to capture neutrons having energies of less than 0.4 eV.

14. The $H_2O$ quantity monitoring device of claim 11 wherein said neutron detecting means includes two neutron detectors said neutron detectors being disposed symetrically about a plane defined by the geometric center of said fast neutron source and the longitudinal axis of said conduit.

15. The $H_2O$ quantity monitoring device of claim 11 wherein:

said moderating means includes a thickness of hydrogenous material interposed intermediate said fast neutron source and said conduit; and, said shielding means includes a thermal neutron absorber interposed intermediate said moderating means and the combination of said conduit and said at least one detector.

16. Apparatus for monitoring the steam quality of a steam-water mixture passing through a conduit, comprising:

a fast neutron source, said fast neutron source being incapable of achieving criticality;

moderating material positioned intermediate said conduit and said fast neutron source, said moderating material having a moderating power equivalent to at least a 1 cm thickness of water;

a neutron detection system including at least one neutron detector, said neutron detection system being adapted to provide an output signal representing the rate of detection of neutrons traversing said at least one neutron detector; and means for affixing said fast neutron source and said at least one neutron detector to said conduit such that said fast neutron source and said at least one neutron detector are maintained in fixed relationship to each other.

17. The steam quality monitoring apparatus of claim 16 wherein said at least one neutron detector is of the type having a neutron detection efficiency inversely related to neutron energy.

18. The steam quality monitoring apparatus of claim 7 further comprising a thermal neutron shield interposed intermediate said moderating material and the combination of said at least one neutron detector and said conduit.

19. The steam quality monitoring apparatus of claim 16 or claim 18 wherein there are two neutron detectors, and wherein a first line joining said neutron detectors is perpendicular to a second line joining the center of said conduit and said neutron source.

20. The steam quality monitoring apparatus of claim 19 wherein said first line intersects the longitudinal axis of said conduit.

21. The steam quality monitoring apparatus of claim 17 further including a neutron reflector positioned around the combination of said fast neutron source, said at least one neutron detector and said conduit.

22. The steam quality monitoring apparatus of claim 21 further including a second thermal neutron shield positioned intermediate said neutron reflector and said neutron detector.

23. A method for monitoring the amount of the liquid phase of a hydrogenous fluid within an enclosure, comprising the steps of:
generating a population of fast neutrons from a fast neutron source, said source being positioned a spaced distance from said enclosure and being free from including a critical mass of fissionable material;
moderating at least a portion of the neutrons reaching the enclosure from the fast neutron source, the degree of moderation being at least equivalent to that of a 1 cm thickness of liquid water;
screening the moderated neutrons at a position intermediate said source and said conduit to remove therefrom substantially all thermal neutrons to obtain a neutron population including epithermal neutrons;
exposing said enclosure to said epithermal neutrons;
detecting neutrons at a first location adjacent to said enclosure; and,
converting, by means of automated processing means, the rate of detection of neutrons into a measure of the amount of said liquid phase within said enclosure.

24. The method of claim 23 further comprising the step of detecting neutrons at a second location adjacent to said conduit.

25. The method of claim 24 where said hydrogenous fluid includes a gas and a hydrogenous liquid, the method further including the steps of monitoring the pressure of the conduit, and determining the mass fraction of hydrogenous liquid within the conduit.

26. The method of claim 24 further including the step of determining the volume fraction of hydrogenous liquid within the conduit.

27. The method of claim 23 wherein said step of converting provides an output directly related to the volume fraction of said enclosure occupied by said liquid phase.

28. The method of claim 23 wherein said step of converting provides an output inversely related to the volume fraction of said enclosure occupied by said liquid phase.

29. The method of claim 23 wherein said step of converting provides an output directly related to the mass fraction of said hydrogenous fluid which is in the liquid phase.

30. The method of claim 23 wherein said step of converting provides an output inversely related to the mass fraction of said hydrogenous fluid which is in the liquid phase.

* * * * *